United States Patent
Kunimoto et al.

[11] Patent Number: 6,126,902
[45] Date of Patent: Oct. 3, 2000

[54] NOX SENSOR

[75] Inventors: Akira Kunimoto; Yongtie Yan; Masaharu Hasei; Hideyuki Kurosawa; Yukio Nakanouchi, all of Kumagaya, Japan

[73] Assignee: Kabushiki Kaisha Riken, Tokyo, Japan

[21] Appl. No.: 08/868,494

[22] Filed: Jun. 3, 1997

[30] Foreign Application Priority Data

Jun. 6, 1996 [JP] Japan ................... 8-165105

[51] Int. Cl.$^7$ ............ G01N 31/12; G01N 27/16; G01N 33/00
[52] U.S. Cl. ............... 422/94; 422/95; 436/116; 436/118
[58] Field of Search .................. 422/94, 95, 96, 422/97, 98; 436/116, 117, 118, 137; 73/23.31, 31.05, 31.06; 204/425, 426, 427; 205/781, 784.5, 783.5, 784, 785

[56] References Cited

U.S. PATENT DOCUMENTS

| | | | |
|---|---|---|---|
| 3,905,918 | 9/1975 | Mai et al. | 252/462 |
| 4,770,760 | 9/1988 | Noda et al. | 204/425 |
| 4,927,517 | 5/1990 | Mizutani et al. | 204/425 |
| 5,034,112 | 7/1991 | Murase et al. | 204/425 |
| 5,192,515 | 3/1993 | Gardner-Chavis et al. | 423/213.2 |
| 5,217,588 | 6/1993 | Wang et al. | 204/426 |
| 5,364,517 | 11/1994 | Dieckmann et al. | 208/121 |
| 5,389,340 | 2/1995 | Satake et al. | 422/98 |
| 5,397,442 | 3/1995 | Wachsman | 73/23.31 |
| 5,672,811 | 9/1997 | Kato et al. | 73/31.05 |

FOREIGN PATENT DOCUMENTS

| | | |
|---|---|---|
| 0678740 | 10/1995 | European Pat. Off. . |
| 0731351 | 9/1996 | European Pat. Off. . |
| 0769693 | 4/1997 | European Pat. Off. . |
| 0769694 | 4/1997 | European Pat. Off. . |

OTHER PUBLICATIONS

Kato et al., "Thick Film ZrO$_2$ NOx Sensor", SAE Technical Paper Series, Feb. 1996, pp. 137–141.

*Primary Examiner*—Alexander Markoff
*Attorney, Agent, or Firm*—Kubovcik & Kubovcik

[57] ABSTRACT

A stable sensor designed to detect accurately the total NOx concentration under 100 ppm in terms of the NO gas concentration is made up of a first cell and a second cell with a gas diffusion aperture provided between the two cells. The first cell has a partition wall of a substrate of oxygen ion conductor containing zirconia as the main component and permitting a gas to be detected to enter the zirconia substrate; oxygen pumping electrodes are also formed on the first cell substrate which functions to expel oxygen in an atmosphere of the first cell to the outside and to reduce NO$_2$ of the NOx gas to be detected to NO gas. While NO gas entering through a gas diffusion aperture between the two cells flows into the second cell, a measurement is made of an electromotive force between a NO detection electrode formed in the second cell and a counter electrode also formed therein or a counter electrode formed on the reverse side of the zirconia substrate, since such electromotive force corresponds to the level of the NO gas concentration and thus provides the total NOx concentration.

6 Claims, 8 Drawing Sheets

NOX SENSOR

BACKGROUND OF THE INVENTION

1. Field of the Invention

The present invention relates to NOx sensors for nitrogen oxides in gas mixtures and more particularly to sensors directly exposed to automotive emissions to measure a total concentration of NOx. The invention is naturally applicable as apparatus for monitoring the NOx concentration of emissions from ordinary manufacturing plants and for environmental monitoring inside tunnels.

2. Description of the Prior Art

Inasmuch as oxides of nitrogen (NOx) in automotive emissions consist essentially of nitrogen monoxide (NO) and nitrogen dioxide ($NO_2$), these two types of gases are subject to detection of the total NOx concentration in the emissions from automotive engines. A construction of a prior-art NOx sensor for detection of automotive emissions which is designed to detect the total NOx concentration is disclosed in FIG. 1 ("Thick Film $ZrO_2$ NOx Sensor" as announced by NGK Insulators, Ltd. in February, 1996 at the Society of Automotive Engineers, Inc.).

It is considered that the following principle underlies the sensor structure in FIG. 1. Namely, partial pressure of oxygen in a first cell 12 (gas flow-in side) in zirconia substrates (having a solid solution of 3–8 mol % Yttrium) 1, 2, 3, 4 is completely diminished to zero or to a constant value by adjustng the voltage of the oxygen pumping electrodes 6a, 6b according to output of oxygen concentration sensors 9a, 9b of the concentration electromotive force type provided at a second cell 13, whereupon only $NO_2$ of the emissions is reduced to NO. Subsequently, NO of the first cell 12 diffuses and flows into the second cell 13, wherein the NO is completely decomposed according to formula (1):

$$NO + 2e^- \rightarrow N + O^{2-} \qquad \ldots (1)$$

Oxygen (ion) which is dissociated then is discharged at second electrodes 16a, 16b to outside the cell. An oxygen ion current obtained at this time is measured to detect the NOx concentration therein. It is to be noted that an electrode voltage appropriate as an oxygen ionization voltage is set up in the second electrodes. Numeral 10 indicates a gas inlet and numeral 11 indicates a gas diffusion aperture. A space 14 between the substrates 2, 4 is a space leading to the atmosphere.

It is basically possible to detect the total NOx concentration of the automotive emissions by using the NOx sensor having the above-mentioned construction in FIG. 1. Nevertheless, there are problems as described hereunder in consideration of the actual situation wherein the sensor thereof is put to use.

Consider first the detection output in accordance with the construction of FIG. 1. The amount of dissociated oxygen through decomposition of NO in the second cell depends on the NOx concentration in the emissions as well as the amount of NO which can flow into a detection cell. The NOx concentration as such in the emissions amounts from 10 ppm to 100 ppm at the most, whereas the issued NOx concentration to be detected in practical use is under 100 ppm in a large number of cases. It must be pointed out that though this method provides the a linear output with the NOx concentration, it is difficult to make an accurate measurement of NOx in the low concentration region below 100 ppm.

Further, the method of FIG. 1 causes an offset since the remainder of oxygen in the second cell directly adds to the sensor output, wherefore there is a restriction that the partial pressure of oxygen inside the second cell be subjected to the control of oxygen partial pressure with an accuracy corresponding to the measurement accuracy (of order of under 1 ppm).

Still further, unless the mode of NO gas diffusion into the second cell is in terms of limiting current because the sensor thereof is of the current detection type, changes in the electrode characteristics will directly affect signal current. That is, output fluctuation with the passage of time is considered to be substantial. In actuality, if the limiting current is to be obtained at the NOx concentration level in the emissions, the output level will be small to a great degree to lessen the plateau output displacement amount further, thus leading to additional reduction of the resolution in measuring gas concentration. Accordingly, the sensor of FIG. 1 is not suitable for practical applications in automotive emissions.

As described above, the problem of the sensors which can directly detect the total NOx concentration in the automotive emissions is the development of stable sensors that can detect, with high accuracy, the total NOx concentration under 100 ppm.

SUMMARY OF THE INVENTION

In view of the foregoing, it is an object of the present invention to provide a sensor which is designed to detect stably a total NOx concentration under 100 ppm with sufficient resolution power.

The sensor according to the invention forms a partition wall with substrates (having a solid solution of 3–8% Yttrium) of an oxygen ion conductor, the main component of which is zirconia, thereby comprising a first cell for an NOx gas or emission gas to be detected to enter the zirconia substrates and a second cell which detects the NOx concentration thereof. Oxygen pumping electrodes are formed in the first cell which is provided with a function to discharge oxygen therein to outside the cell and to reduce $NO_2$ in the NOx gas to NO gas. The sensor of the present invention is also characterized in that the NO gas passing through a gas diffusion aperture between the first cell and the second cell, is subjected to measurement of electromotive force between an NO detection electrode formed inside the second cell and a counter electrode formed therein or on a reverse side of the zirconia substrate to detect the total NOx concentration of the emissions to be detected.

Also, the above-mentioned NOx sensor is characterized by a construction, wherein, together with the oxygen pumping function of the first cell, a catalytic electrode which reduces $NO_2$ to NO is formed on the oxygen pumping electrodes or separately on the zirconia substrate inside the cell, and that an NO detecting electrode material in the second cell comprises oxide compounds of the perovskite type and spinel type including Mn as a constituent element.

The sensor of the present invention can measure the total NOx concentration according to the following principle of detection: First, while holding the partial pressure of oxygen in the cells (the first cell and the second cell) constant by means of the oxygen pumping electrodes in the first cell provided in the sensor substrate, adjustment of catalytic electrode voltage on the oxygen pumping electrodes or the pumping electrodes reduces only $NO_2$ in the emissions to NO.

NO in the first cell passes through the diffusion aperture, diffuses and flows into the second cell, wherein an oxidation reaction of a formula (2) is considered to occur on the NO detection electrode.

$$NO + O^{2-} \rightarrow NO_2 + 2e^-  \qquad \ldots (2)$$

That is, in the sensor of the invention, the total NOx concentration is measured as the electromotive force corresponding to the NO gas concentration. The sensor of the electromotive force type is advantageous in that so long as the measuring current falls within a certain limit in the same manner as ordinary cells, that is, when a sensor output impedance is relatively small as compared to an input impedance of a sensor output measuring circuit, the sensor electromotive force is not changed. Consequently, despite changes to some extent in the reaction constant of the detection electrode and the effective area of the electrode, the electromotive force as such can be considered to be stable.

In the electromotive force type sensor, electromotive force in the sensor is basically a difference of chemical potential between the detection electrode and the counter electrode. In the sensor according to the present invention, as is clear from the detection reaction, a potential difference accompanying oxygen ion between the electrodes becomes electromotive force of the sensor. IN the sensor construction of FIG. 2, the oxygen concentration of the counter electrode is fixed so that the sensor is subject to changes of the oxygen partial pressure in the second cell, while in the sensor construction of FIG. 7, the NO detection electrode and the counter electrode are provided in the second cell so that despite changes in the oxygen concentration in the second cell, such influence can be canceled. Therefore, as far as partial pressure control of oxygen in the second cell is concerned, there is an advantage in that it is only necessary for the lower limit of the minimum necessary oxygen concentration (approximately 500 ppm) to be met. This enables the accuracy which is required of the oxygen sensor controlling the oxygen concentration in the second cell to be relaxed considerably, a great advantage in terms of sensor reliability.

The specific nature of the invention, as well as other objects, uses and advantages thereof, will clearly appear from the description and from the accompanying drawings, in which:

DETAILED DESCRIPTION OF PREFERRED EMBODIMENTS

Figure 1:
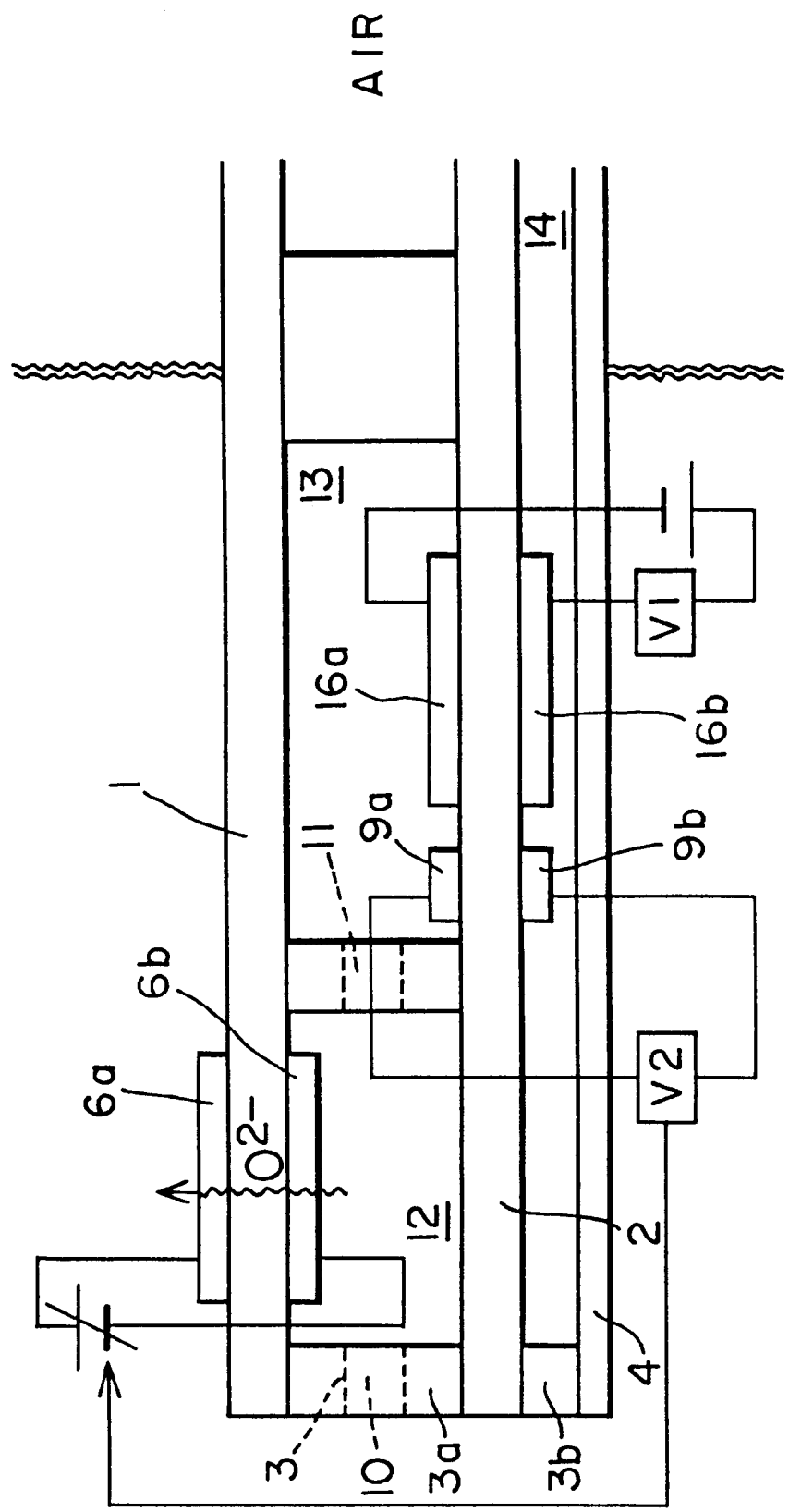
FIG. 1 is a schematic sectional view of a total NOx sensor conventionally proposed.
Figure 2:
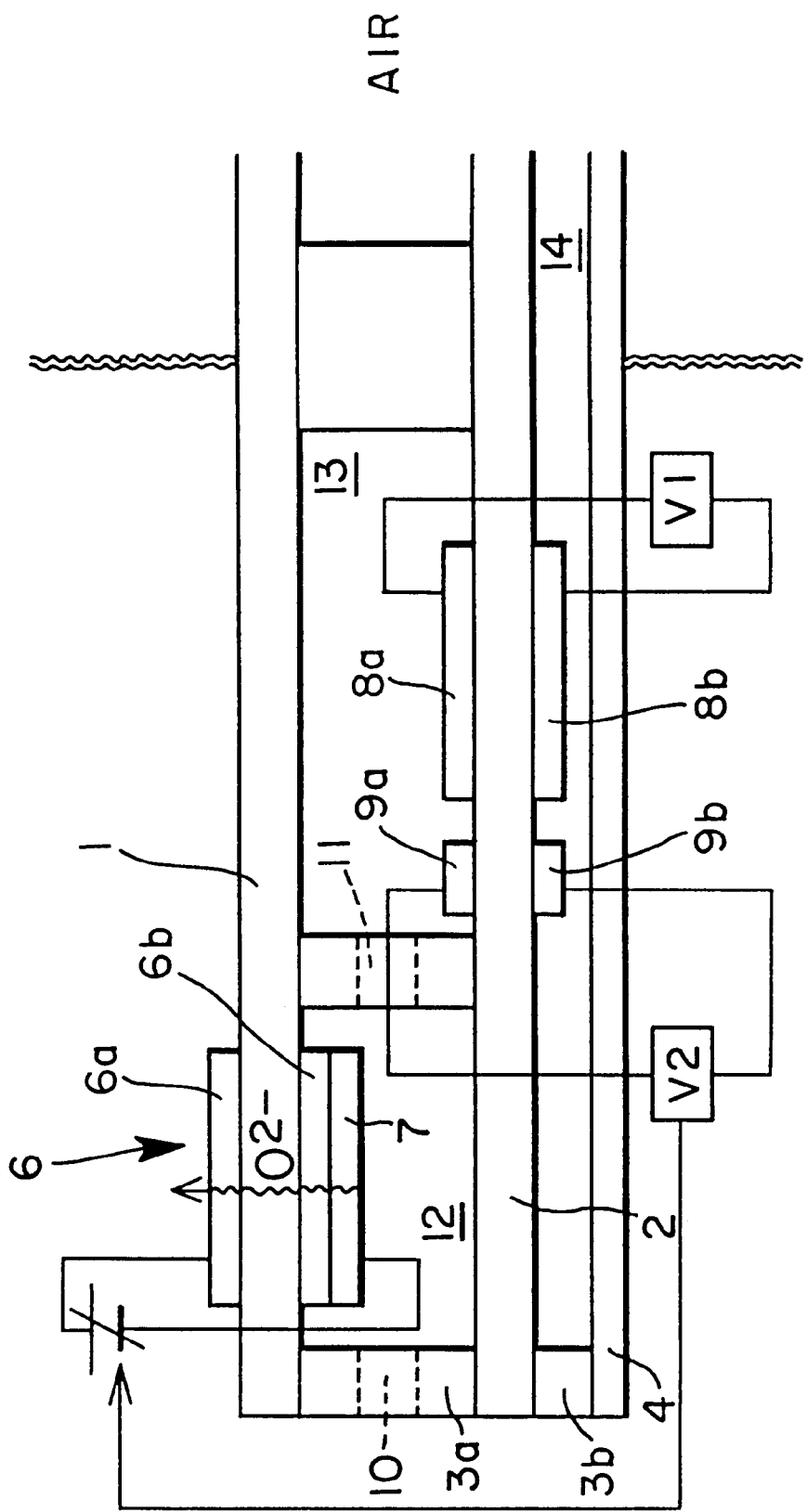
FIG. 2 is a schematic sectional view of a total NOx sensor according to the present invention.
Figure 3:
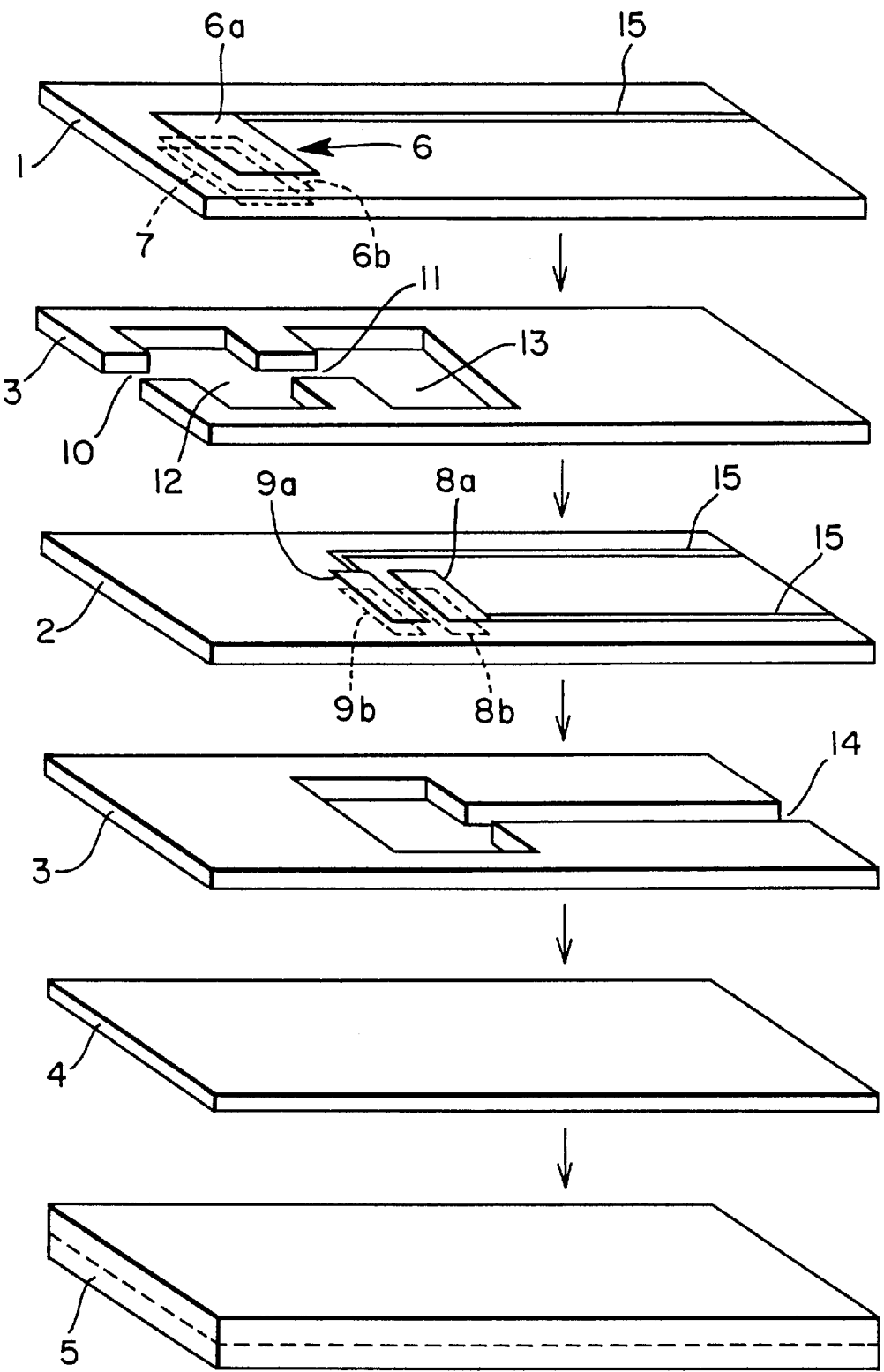
FIG. 3 is an exploded structural view of the total NOx sensor according to the present invention.

A specific example of the sensor construction of the invention is a layered structure of zirconia substrates shown in FIGS. 2 and 3. Referring to FIGS. 2 and 3, oxygen ion conductor substrates are shown by 1, 2, and 3,4, and yttria-added zirconium substrates can be generally used. Also, 3a and 3b are separate to form reaction cells 12 (the first cell) and 13 (the second cell) in between zirconia substrates 1, 2. The spacers 3a, 3b are preferably made up of zirconia which is advantageous in terms of thermal expansion, but formation thereof is possible with glass printed layers. In the case of the former, there are two methods: one is that of punching zirconia green sheets which are subjected to laminated bonding by pressing, then succeeded by one-piece baking; and the other is that of punching baked zirconia substrates by means of sand blasting or other methods, thereafter each substrate being seal bonded by glass.

Oxygen pumping electrodes 6a (anode) and 6b (cathode) are formed at the position of the first cell 12, both 6a and 6b being generally formed at Pt printing electrodes. Exhaust gas flows in the exhaust gas inside the cell (12 and 13) is discharged to outside the cells by means of the oxygen pumping mechanism of the cell 12. Voltage to be applied on the electrodes 6 is adjusted to ensure that only $NO_2$ of the exhaust gas is reduced to NO while partial pressure of such in-cell oxygen is in the state of being lowered.

After reduction only to NO in the first cell, the NO flows through a gas diffusion aperture 11 to the second cell 13, where the NO concentration in the cell 13 is detected due to a difference in electromotive force between a detection electrode 8a, sensitive to NO gas, and a counter electrode 8b formed by sandwiching the substrate 2 therebetween. Use of metal oxide compounds of perovskite, and spinal types containing MN, enables the NO concentration to be measured accurately without being affected by the conventional drawback of $NO_2$ interference characteristics.

When a baked zirconia substrate (containing 3–8 mol % Yttrium) is used for the substrate to form a detection electrode film on it, the electrode film can be formed by normal sputtering. When a sensor is made by green sheet baking, after the process of coating the electrode films with screen printing and drying, the sheets are press bonded and baked. Inasmuch as the detection reaction of NO is an oxidation reaction as shown by the formula (2), it is impossible to lower the oxygen partial pressure in the cell 13 to zero. Consequently, an oxygen sensor of concentration cell type (9a, 9b) juxtaposed in the cell 13 performs control of the partial pressure of oxygen in the cell 13 (12) at all times. As regards the partial pressure of oxygen in the second cell, so long as the amount of oxygen sufficient to react with the NOx concentration in terms of stoichiometry is available, that is adequate.

Note, however, that since the partial pressure of oxygen in the first cell 12 must be controlled simultaneously, it is necessary for the oxygen concentration to be on such a level that the $NO_2$ reduction in the cell 12 will be held under the electrolysis voltage (1.2 V) of water. As a result of this requirement, feed back control by the oxygen sensor output is conducted to keep the in-cell oxygen concentration to a level of 500 ppm to 5000 ppm. Moreover, to decrease the pumping voltage at the time of $NO_2$ reduction in the cell 12, it is effective to form on a pumping cathode electrode a catalytic electrode 7. As a material for the catalytic electrode, a thin film of the noble metal type or metal oxide type is layer-coated over the electrode 6b. 14 indicates a space leading to the atmosphere.

First Embodiment of the Invention

For a demonstration of the effect of the present invention, a sensor of a structure illustrated in FIG. 3 was manufactured. First, on a 2-inch four-cornered substrate (0.2 mm thick) to which yttria of 8 mol % was added and which underwent baking beforehand, spacers 3a and 3b were opened by sand blasting at illustrated positions within the dimensions of a sensor substrate (6 mm×45 mm). In this condition, on both sides of the sensor substrate 1 were simultaneously printed at Pt lead pattern and oxygen pumping electrodes 6a and 6b by means of screen printing, which, after drying, were treated with baking at 950° C. for one hour. However, as for the sensor substrate 2 having no formation of a catalytic electrode 7 thereon, first, as electrodes 9a and 9b for oxygen sensor, a Pt paste was printed, together with a counter electrode 8b and a lead pattern 15, by means of screen printing, then baking was conducted at 1050° C. Thereafter, a thin-film electrode of $CuMn_2O_4$ was formed as an NO detection electrode 8a on the same substrate 2. For formation of the electrode 8a, RF magnetron sputtering was employed. For the sputter target, a $CuMn_2O_4$ powder target was used. The film-depositing conditions by sputtering were a sputter gas of Ar at a pressure of 1 Pa, sputtering RF power of 150 W, substrate heating at 200° C., and a deposited film thickness of 4000 Å. At this stage, the 2-inch substrate was cut to the size of each sensor substrate. Substrates 1, 2, 3, and 4 were printed by glass paste, bonded together, and subjected to glass baking which was conducted at 900° C. for one hour, whereupon the combined piece was bonded to the sensor substrate by a inorganic material bond at a non-heating part of a separately-made alumina heater substrate 5.

The sensor manufactured in this manner was inserted into a quartz tube set in the electric furnace (400° C.) and the gas sensitivity characteristics thereof was verified according to the following procedure. It is to be noted that heater control was performed to keep the sensor temperature at approximately 700° C., and that the oxygen concentration in the sensor cell was controlled to be approximately 2000 ppm.

Measurement A was conducted with $O_2$ of 4% and $N_2$ balance as the base gas to which NO gas was introduced to form a gas composition of 20 to 500 ppm, whereupon the concentration dependency upon NO gas was examined.

Figure 4:
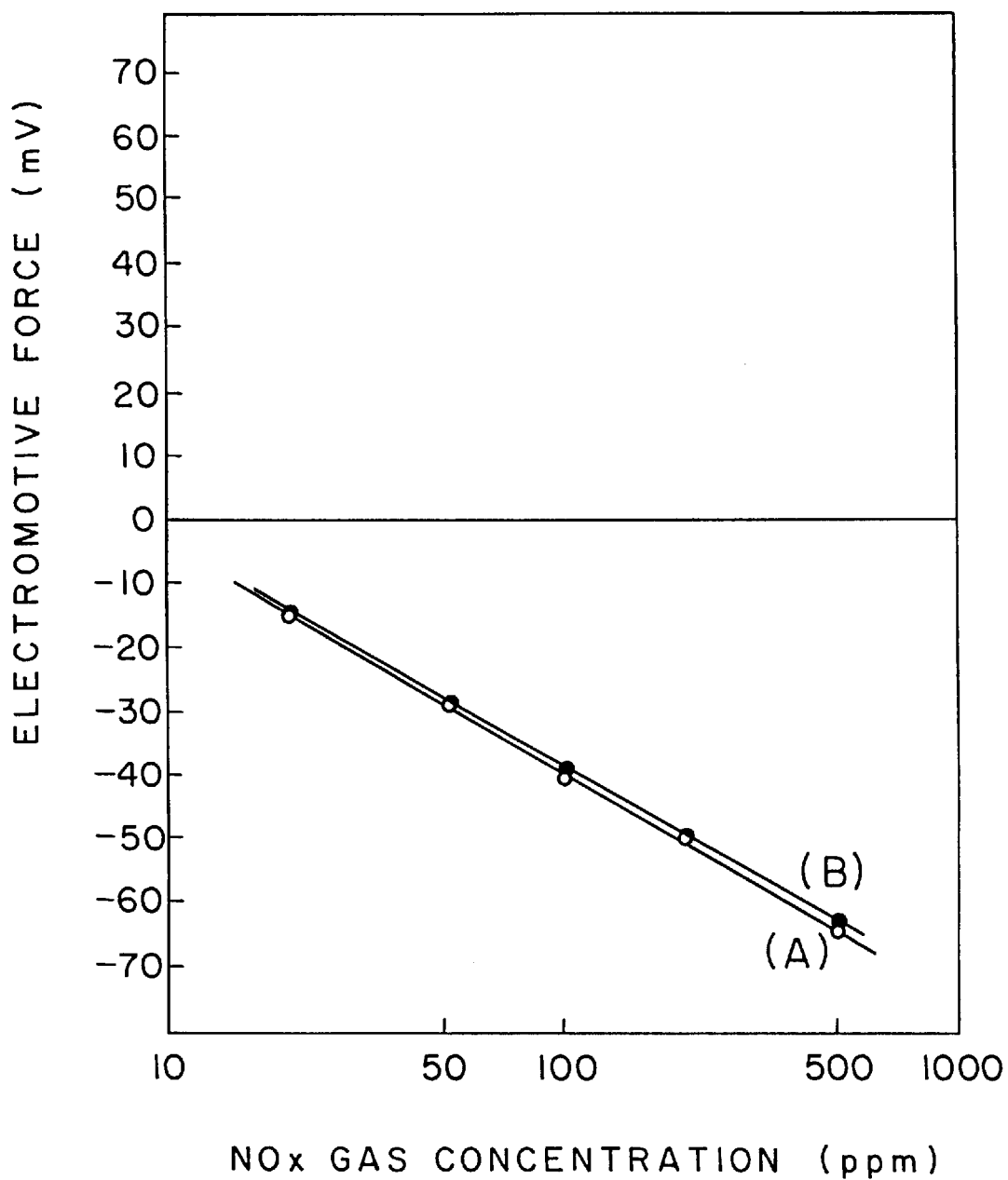
FIG. 4 is a graph showing the NO and $NO_2$ detection characteristics of the total NO x sensor according to the present invention.
Figure 5:
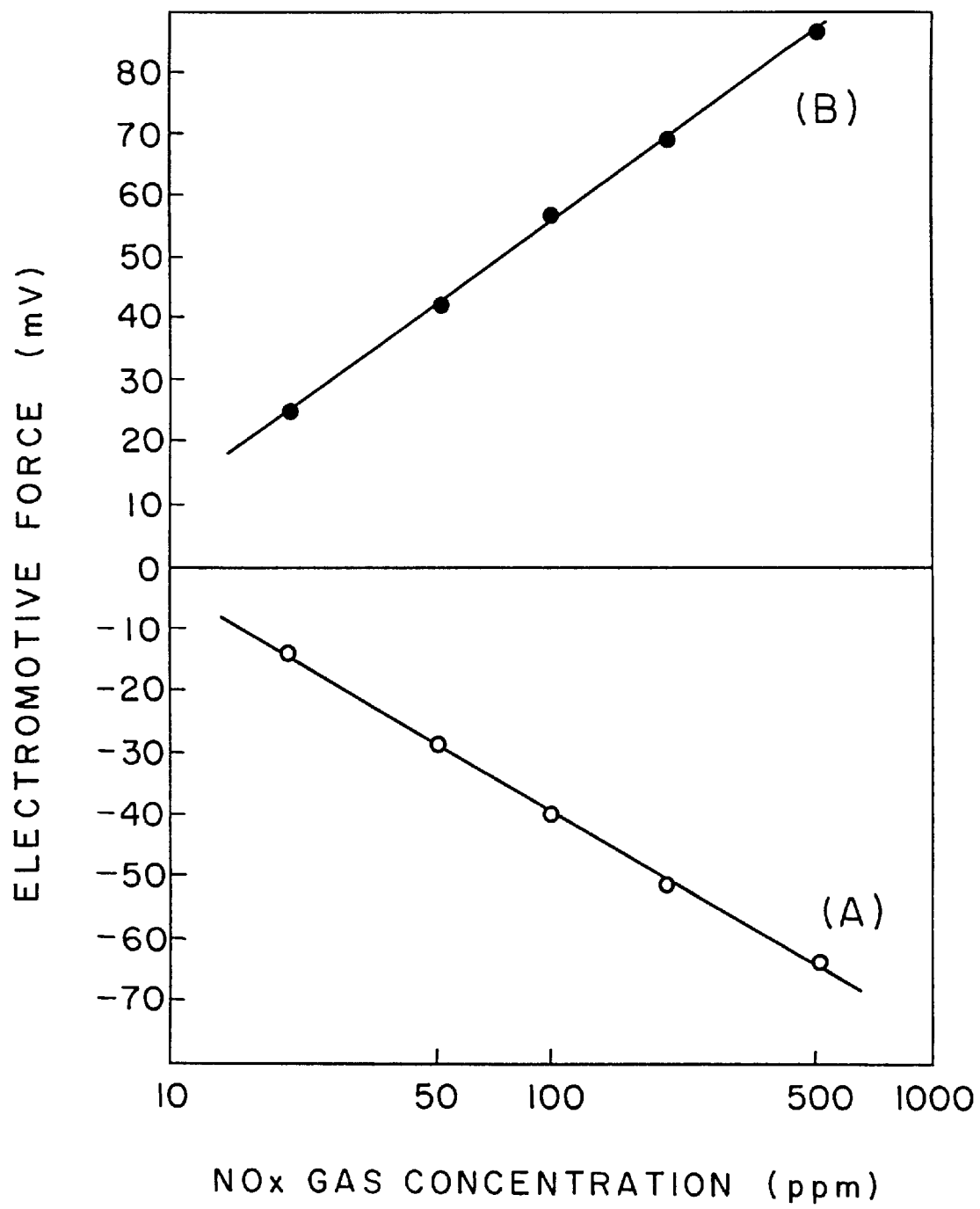
FIG. 5 is a graph of showing the original NO and $NO_2$ detection characteristics of a detection electrode employed in the first embodiment.

Measurement B was conducted with $O_2$ of 4% and $N_2$ balance as the base gas to which $NO_2$ gas was introduced to form a gas composition of 20 to 500 ppm, whereupon the concentration dependency upon $NO_2$ gas was examined. Results obtained are shown together in FIG. 4. Results obtained after measuring in the same manner in regard to only the substrate 2 are shown in FIG. 5. As clear from the results therein, $NO_2$ in NOx of the sensor structure according to the present invention is substantially completely reduced to NO, showing that said sensor is operating as the total NOx sensor. Further, as shown clearly from the characteristics of gas concentration dependency of sensor electromotive force, a sufficiently large value of approx. 40 mV is obtained in a low gas concentration region of 100 ppm. Therefore, resolution capacity of an order of 10 ppm is sufficiently satisfied.

Second Embodiment

Figure 6:
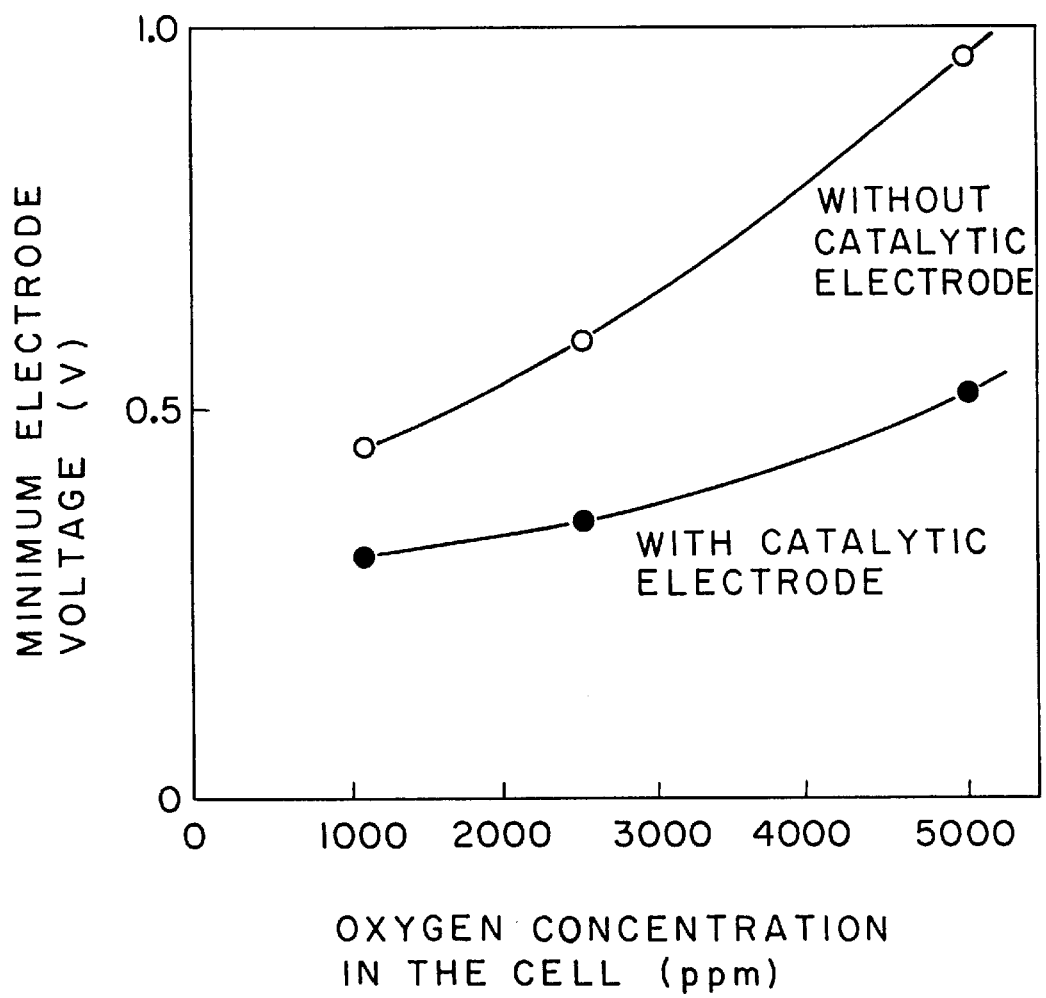
FIG. 6 is a graph showing the effect of a catalytic electrode of the first cell in the second embodiment.

A sensor was manufactured in the same way as the first embodiment, although in this case, $LaRuO_3$ was layered as a catalytic electrode by print-forming on the cathode of the oxygen pumping electrodes in the first cell. Baking of the catalytic electrode thereof was conducted simultaneously with the baking of a base Pt electrode. Evaluation at this point was made by checking the influence on the complete decomposition voltage of $NO_2$ by changing the in-cell oxygen concentration to 2000 to 10000 ppm, namely, changes in the oxygen pumping. (catalyzer) electrode voltage when a deviation of (B) from (A) occurs in FIG. 4. As the results show in FIG. 6, the electrode voltage can be small even at the same oxygen concentration as that of forming the catalytic electrode. This is effective in expanding the upper limit of the in-cell oxygen concentration. Hence, it can be said that stability of the detection electrode which uses oxidation reaction will increase, and that there is some reserve created in control of the in-cell oxygen concentration.

Third Embodiment

Figure 7:
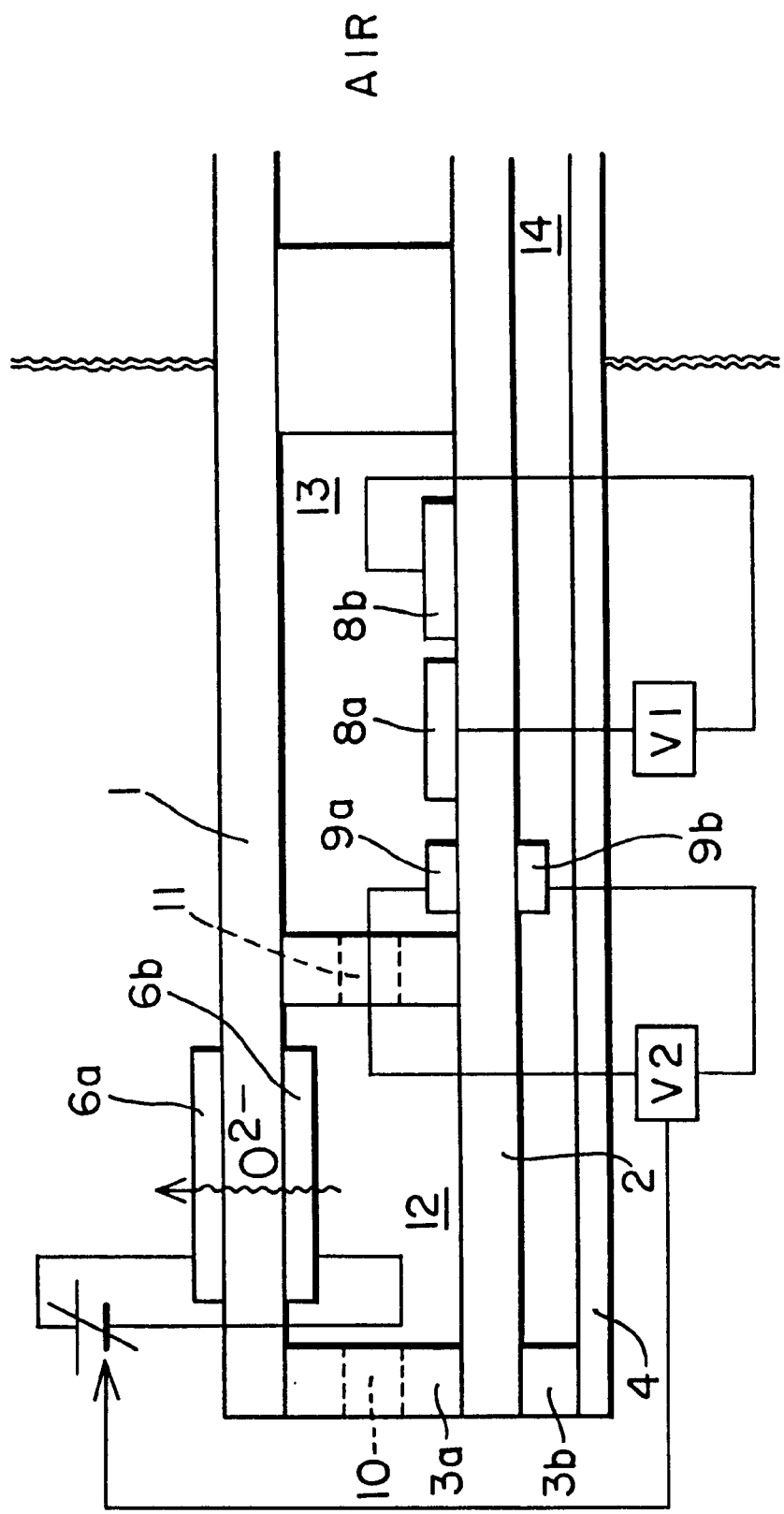
FIG. 7 is a schematic sectional view of the total NOx sensor according to the present invention.
Figure 8:
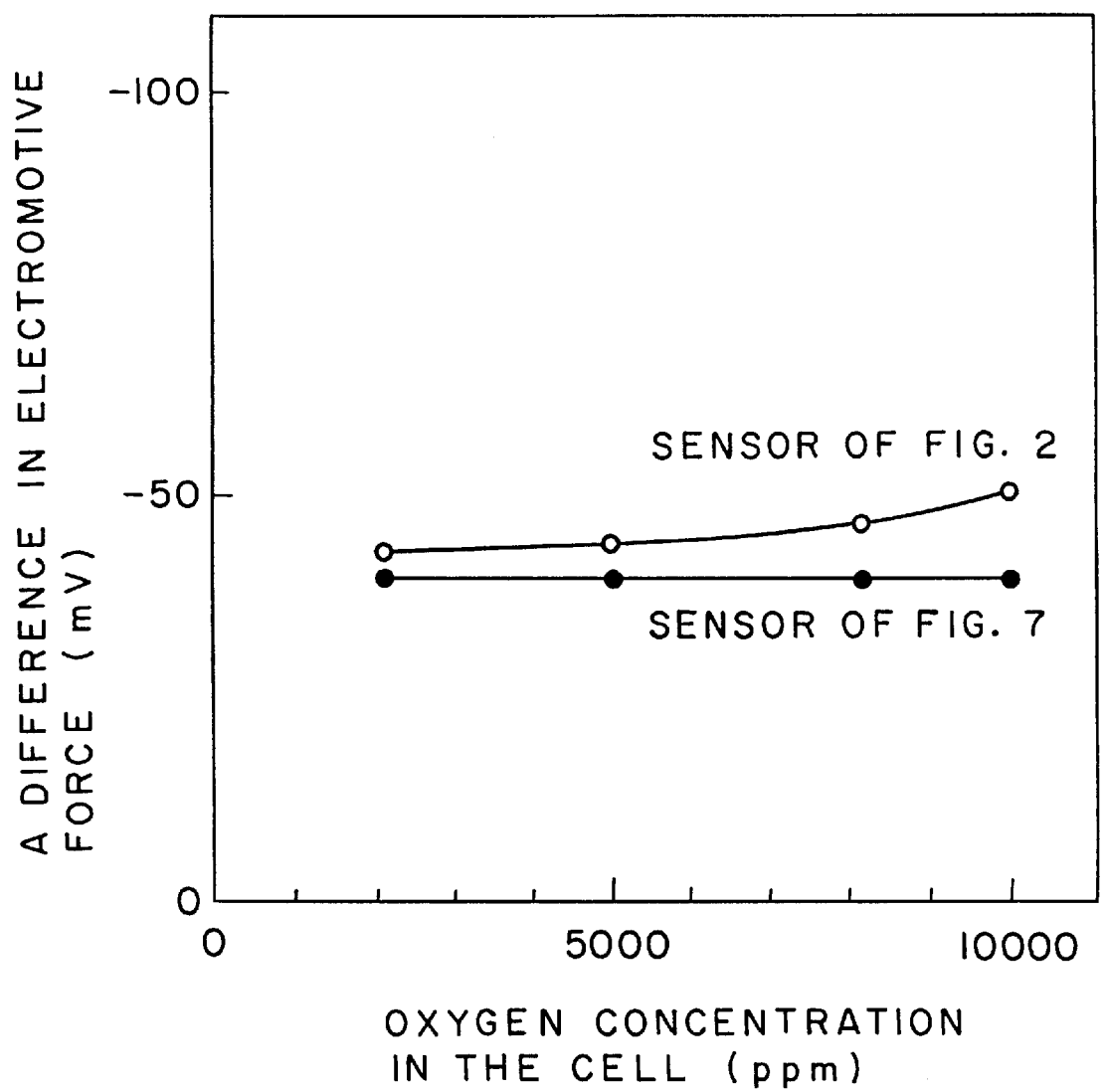
FIG. 8 is a graph showing the effect of an arrangement of a counter electrode in the third embodiment.

A sensor of the structure shown in FIG. 7 was manufactured in the same way as the first embodiment, and a comparison of the degree of influence upon the sensor electromotive force of the in-cell oxygen concentration according to the sensor structure of FIG. 2 was made. By changing the in-cell oxygen concentration to 2000 to 10000 ppm, the sensor electromotive force with respect to 100 ppm NO gas was measured. Results are shown in FIG. 8, making it known that with the sensor structure of FIG. 7, the in-cell oxygen concentration hardly affects the sensor output over a range of 2000 to 10000 ppm. On the other hand, when the counter electrode is used as atmospheric standards, oxygen concentrations of 2000 ppm and 5000 ppm as the output fluctuation produced a fluctuation of approximately 9% of NO detecting output.

A procedure wherein for purposes of detecting the total NOx concentration under 100 ppm in the condition of a mixture of NO and $NO_2$ as in the case of automotive emissions, $NO_2$ is reduced to NO in the first cell of the sensor substrate, and wherein detection of the NO is conducted by the electromotive force type electrode in the second cell is highly effective since such procedure contributes to increasing the gas concentration resolution power in the low gas concentration region, that is, a sensor structure suited to be mounted directly on automobiles and other vehicles for detection of NOx in emissions.

The foregoing invention has been described in terms of preferred embodiments. However, those skilled in the art will recognize that many variations of such embodiments exist. Such variations are intended to be within the scope of the present invention and the appended claim.

What is claimed is:

1. A sensor for detecting a total concentration of NOx in a gas mixture to be detected, comprising:
   first and second cells having partition walls formed of a substrate of an oxygen ion conductor containing zirconia as a main component thereof, the gas mixture to be detected flowing between said partition walls;
   a gas diffusion aperture separating said first and second cells and through which the gas mixture can diffuse and flow from said first cell into said second cell;
   said first cell having oxygen pumping electrodes on opposite sides of one of said partition walls thereof for discharging oxygen therein to the outside of the first cell and reducing $NO_2$ of the NOx in said gas mixture to NO gas to produce a total concentration of NO gas and to maintain an oxygen concentration in said gas mixture of more than about 500 ppm and sufficient to react with the total concentration of NO gas in the gas mixture; and
   said second cell being positioned next to said first cell to detect the total concentration of NOx by measuring the total concentration of NO gas and comprising an NO detection electrode and a counter electrode formed inside said second cell, said NO detection electrode comprising a material which enables oxidation reaction between said NO and oxygen present on the NO detection electrode, and said NO detection electrode and counter electrode generating an electromotive force therebetween indicative of the concentration of the oxidized NO gas.

2. A sensor for detecting a total concentration of NOx in a gas mixture to be detected, comprising:

first and second cells having partition walls formed of a substrate of an oxygen ion conductor containing zirconia as a main component thereof, the gas mixture to be detected flowing between said partition walls;

a gas diffusion aperture separating said first and second cells and through which NO gas can diffuse and flow from said first cell into said second cell;

said first cell having oxygen pumping electrodes on opposite sides of one of said partition walls thereof for discharging oxygen therein to the outside of the first cell and reducing $NO_2$ of the NOx in said gas mixture to NO gas to produce a total concentration of NO gas and to maintain an oxygen concentration in said gas mixture of more than about 500 ppm and sufficient to react with the total concentration of NO gas in the gas mixture; and said second cell being positioned next to said first cell to detect the total concentration of NOx by measuring the total concentration of NO gas and comprising an NO detection electrode and a counter electrode formed on an inner surface and an outer surface, respectively, of a partition wall of said second cell, and a means for measuring an electromotive force generated between said NO detection electrode and said counter electrode without application of voltage therebetween, said NO detection electrode comprising a material which enables oxidation reaction between said NO and oxygen present on the NO detection electrode, and said NO detection electrode and counter electrode generating said electromotive force therebetween indicative of the concentration of the oxidized NO gas.

3. The sensor of claim 1, wherein said first cell further comprises a catalytic electrode for reducing $NO_2$ to NO formed on an oxygen pumping electrode inside said first cell.

4. The sensor of claim 2, wherein said first cell further comprises a catalytic electrode for reducing $NO_2$ to NO formed on an oxygen pumping electrode inside said first cell.

5. The sensor of claim 1, wherein said NO detection electrode is a perovskite composite oxide or a spinel composite oxide containing Mn.

6. The sensor of claim 2, wherein said NO detection electrode is a perovskite composite oxide or a spinel composite oxide containing Mn.

* * * * *